United States Patent [19]
Guder et al.

[11] Patent Number: 5,254,677
[45] Date of Patent: Oct. 19, 1993

[54] β-GALACTOSIDASE SUBSTRATES FOR CEDIA

[75] Inventors: Hans-Joachim Guder; Ruppert Herrmann, both of Weilheim; Dietmar Zdunek, Munich, all of Fed. Rep. of Germany

[73] Assignee: Boehringer Mannheim GmbH, Mannheim, Fed. Rep. of Germany

[21] Appl. No.: 720,306

[22] Filed: Jun. 25, 1991

[30] Foreign Application Priority Data

Jul. 3, 1990 [DE] Fed. Rep. of Germany ....... 4021063

[51] Int. Cl.$^5$ .......... C07G 3/00; C07H 15/00; B01N 33/567; C12Q 1/48
[52] U.S. Cl. .................. 435/7.9; 435/18; 536/4.1
[58] Field of Search .......... 536/4.1, 28, 17.9, 18, 536/53; 435/11, 7.5, 18, 7.9; 514/409, 183, 63; 71/93; 436/505

[56] References Cited

U.S. PATENT DOCUMENTS

| | | | |
|---|---|---|---|
| 4,228,274 | 10/1980 | Ponpipom et al. | 536/17.9 |
| 4,708,929 | 11/1987 | Henderson | 435/7.5 |
| 4,959,324 | 9/1990 | Ramel et al. | 435/11 |
| 4,985,448 | 1/1991 | Zilch et al. | 514/409 |

FOREIGN PATENT DOCUMENTS

| | | |
|---|---|---|
| 0263435 | 4/1988 | European Pat. Off. . |
| 0292169 | 11/1988 | European Pat. Off. . |
| 0413561 | 2/1991 | European Pat. Off. . |
| 86/02666 | 5/1986 | PCT Int'l Appl. . |

*Primary Examiner*—Michael G. Wityshyn
*Assistant Examiner*—Louise N. Leary
*Attorney, Agent, or Firm*—Nikaido, Marmelstein, Murray & Oram

[57] ABSTRACT

The present invention provides compounds of the general formula:

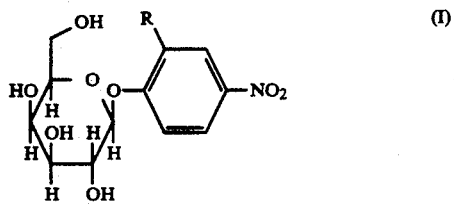

wherein R is a trifluoromethyl radical or a cyano group. The present invention also provides processes for the preparation of these compounds, as well as reagents containing them. The present invention is also concerned with the use of these compounds as β-galactosidase substrates, especially in a CEDIA system.

8 Claims, No Drawings

β-GALACTOSIDASE SUBSTRATES FOR CEDIA

The present invention is concerned with new β-galactosidase substrates for CEDIA, processes for the preparation thereof and reagents for the detection of an analyte in a sample solution with a CEDIA system.

The measurement of low concentrations of analytes in body fluids, for example blood, serum or urine, requires very sensitive test methods, such as are provided, for example, by immunoassays. The detection system of certain immunotests depends upon the fact that, in the detection step, the reaction of the labelling enzyme β-galactosidase takes place with a chromogenic enzyme substrate. The extinction of the liberated coloured material then waives a direct indication of the amount of the analyte to be determined. For the achievement of high sensitivity, the use of sensitive enzyme substrates is necessary which satisfy the test-specific requirements of the test not only with regard to their enzymatic cleavage but also in the spectral properties of the chromophor to be liberated.

CEDIA depends upon the association of two enzymatically inactive β-galactosidase fragments to give an active total enzyme. These two fragments, a so-called enzyme donor and an enzyme acceptor, can be prepared by gene-technological processes. Donors and acceptors suitable for CEDIA are described in U.S. Pat. No. 4,708,929.

CEDIA (cloned enzyme donor immunoassay) depends upon the fact that a hapten is bound covalently to the enzyme donor, namely, in such a manner that the spontaneous reassociation of the enzyme fragments to give an active enzyme is not hindered. However, in the case of binding of a hapten-specific antibody to the conjugate of hapten and enzyme donor, the complementation of enzyme donor and acceptor is inhibited. Thus, the hapten-specific antibody regulates the amount of active β-galacosidase formed. This is quantitatively determined photometrically by the hydrolysis of appropriate chromogenic substrates. A more detailed description of the CEDIA system and of its possible use is to be found in an article by Khanna and Worthy in American Clinical Laboratory, October, 1989.

The criterion for the quality of a chromogenic substrate for CEDIA is expressed on the basis of the dynamic measurement range which can be described especially by the gradient of a calibration curve resulting by two calibrators. For this purpose, it is important that the substrate (a) has a high extinction coefficient and (b) has a high enzymatic cleavage rate by β-galactosidase.

U.S. Pat. No. 4,708,929 discloses 2-nitrophenyl-β-D-galactopyranoside as a chromgenic enzyme substrate for CEDIA. However, its low sensitivity is a considerable disadvantage of this substrate. Therefore, there is a need to develop improved chromogenic substrates for the determination of low concentrations of analytes in a solution.

2-Halo-4-nitrophenylgalactosides are described in published European Patent Specification No. EP-A 0,292,169 as improved β-galactosidase substrates. However, these compounds were not considered for use in CEDIA.

It is an object of the present invention to provide new and improved β-galactosidase substrates, especially for use in CEDIA.

Thus, according to the present invention, there are provided new and improved β-galactosidase substrates of the general formula:

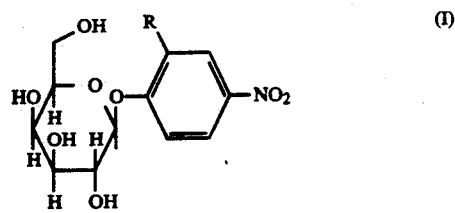

wherein R is a trifluoromethyl radical or a cyano group.

The new compounds according to the present invention are designated as 2-trifluoromethyl-4-nitrophenyl-β-D-galactopyranoside and 2-cyano-4-nitrophenyl-β-D-galactopyranoside.

The present invention also provides a process for the preparation of the compounds of general formula (I). It is preferred to start from a compound of the general formula:

wherein R is a trifluoromethyl radical or a cyano group. A nitro group is introduced into this compound of general formula (II) in the p-position to the hydroxyl group on the aromatic ring to give a compound of the general formula:

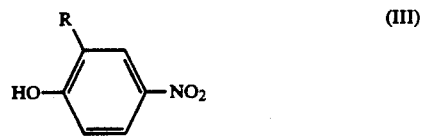

wherein R has the same meaning as above. The compound of general formula (III) can subsequently be reacted with silver oxide and acetobromogalactose, an acetylated β-D-galactopyranoside thereby being obtained. By splitting off the acetyl radical, there is obtained the end product of general formula (I).

For the preparation of 2-trifluoromethyl-4-nitrophenyl-β-D-galactopyranoside, 2-trifluoromethylphenol is first nitrated with concentrated nitric acid and the resultant 2-trifluoromethyl-4-nitrophenol is recovered. This is reacted with silver oxide and acetobromogalactose. By means of this reaction, there is obtained an acetylated product which, by treatment with an alkali, for example sodium methylate, can be converted into the desired end product by splitting off the acetyl radical.

2-Cyano-4-nitrophenyl-β-D-galactopyranoside can be obtained by a similar process. For this purpose, 2-hydroxybenzonitrile is used as starting material which is reacted with a mixture of concentrated sulphuric and nitric acids to give 2-hydroxy-5-nitrobenzonitrile. The resultant product is again reacted with silver oxide and acetobromogalactose, an acetylated intermediate thereby being formed. From this, the desired end product is again obtained by splitting off the acetyl radical.

The compounds according to the present invention are especially suitable for use as β-galactosidase substrates. It is thereby especially preferred when the β-galactosidase consists of two polypeptide fragments which are only enzymatically active in the case of association, whereas alone they possess substantially no enzymatic activity. By "substantially no enzymatic activity" is to be understood that the enzymatic residual activity of the individual β-galactosidase fragments is too small for an interference with the CEDIA. Such β-galactosidase donor and acceptor fragments are disclosed in U.S. Pat. No. 4,708,929. Most preferred is the use of the compounds according to the present invention as β-galactosidase substrates in a CEDIA system. The best results are thereby given in a T4-CEDIA test, in which thyroxine T4 is used as hapten bound covalently to the enzyme donor (see U.S. Pat. No. 4,708,929).

The present invention also provides a process for the detection of an analyte in a sample solution with a CEDIA system in which, as detection enzyme, there is used β-galactosidase and, as β-galactosidase substrate, 2-trifluoromethyl-4-nitrophenyl-β-D-galactopyranoside and/or 2-cyano-4-nitrophenyl-β-D-galactopyranoside.

Furthermore, the present invention provides a reagent for the determination of an analyte with a CEDIA system, wherein 2-trifluoromethyl-4-nitrophenyl-β-D-galactopyranoside and/or 2-cyano-4-nitrophenyl-β-D-galactopyranoside is used as β-galactosidase substrate.

If the new substrates according to the present invention are compared with the hitherto used o-nitrophenyl-β-D-galactopyranoside, it is found that the substrates according to the present invention are clearly superior to the substrate according to the prior art with regard to the enzymatic cleavage rate and to the sensitivity.

It has also been ascertained that the substrates according to the present invention are superior to the 2-chloro-4-nitrophenyl-β-D-galactopyranoside according to European Patent Specification No. EP-A-0,292,169.

The following Examples are given for the purpose of illustrating the present invention:

EXAMPLE 1

Preparation of
2-cyano-4-nitrophenyl-β-D-galactopyranoside 1) 2-Hydroxy-5-nitrobenzonitrile A solution of 70 ml. 40% nitric acid and 10 ml. concentrated sulphuric acid is added dropwise at 10° C. in the course of 1 hour to 24 g. (0.2 mole) 2-hydroxybenzonitrile in 20 ml. water. The reaction mixture is subsequently stirred for 24 hours at 20° C. and then shaken out with 100 ml. ethyl acetate. After evaporation of the organic solvent, the solid residue obtained is extracted twice with 500 ml. amounts of boiling n-hexane. Purification takes place by means of column chromatography on silica gel (silica gel 60; elution agent ethyl acetate). After evaporation of the solvent and crystallisation from ethyl acetate/toluene, there are obtained 2 g. of the desired product in the form of white crystals.

TLC (silica gel 60; ethyl acetate): RF=0.11 UV spectrum (in 0.1M potassium phosphate buffer pH 7.0): $\lambda_{max}$=376 nm ($\epsilon$=15700 l/mol. cm.).

2)
2-Cyano-4-nitrophenyl-2,3,4,6-tetra-O-acetyl-β-D-galactopyranoside

A solution of 1 g. (6.1 mmole) 2-hydroxy-5-nitrobenzonitrile in 200 ml. dry acetonitrile is mixed with 1.5 g. (6.6 mmole) silver oxide and stirred for 3 hours at 20° C. Subsequently, at the same temperature, a solution of 2.7 g. (6.6 mmole) acetobromogalactose in 80 ml. dry acetonitrile is added thereto and the reaction mixture is stirred for 16 hours at ambient temperature. The silver salts are filtered off over a Seitz filter and the filtrate is evaporated to dryness. The crude product obtained is recrystallised from acetone/water. Yield 2.9 g. (96% of theory). TLC (silica gel 60; toluene/ethyl acetate 2:1 v/v): RF=0.27.

3) 2-Cyano-4-nitrophenyl-β-D-galactopyranoside 2.9 g. (5.8 mmole) of the acetylated product from 2) are dissolved in 10 ml. anhydrous methanol and mixed with 4 ml. of a saturated solution of sodium methylate. The reaction mixture is stirred at 20° C. until the reaction is complete (about 1 hour, TLC monitoring), the precipitate is filtered off, washed with a little cold methanol and dried in a vacuum at 40° C. Yield 1.0 g. (53% of theory).

TLC (silica gel 60; chloroform/methanol 3:1 v/v): RF=0.35

$^1$H-NMR (100 mHz, DMSO-d$_6$): δ (ppm)=8.70 (d, J=3 Hz; 1H), 8.49 (dd, J=3 Hz, 9 Hz; 1H), 7.55 (d, J=9 Hz, 1H), 5.36–5.26 (m, 2H), 4.94 (d, J=7 Hz, 1H), 4.70–4.60 (m; 2H), 3.75–3.40 (m, 6H).

Mass spectrum: m/e=326 (neg. FAB).

EXAMPLE 2

Preparation of
2-trifluoromethyl-4-nitrophenyl-β-D-galactopyranoside 1) 2-Trifluoromethyl-4-nitrophenol 20 ml. (0.18 mole) 40% aqueous nitric acid are added to a suspension of 10 g. (0.06 mole) 2-trifluoromethylphenol in 30 ml. water with ice cooling and within the course of 1 hour. Stirring is continued for 2 hours at 20° C., followed by shaking out with 100 ml. ethyl acetate. After drying the organic phase over anhydrous sodium sulphate, the solvent is stripped off on a rotary evaporator and the product obtained purified by means of column chromatography over silica gel (silica gel 60; elution agent ethyl acetate/petroleum ether: 1:3 v/v).

TLC (silica gel 60; ethyl acetate/toluene 1:2 v/v): RF=0.44.

The fractions are collected and evaporated under vacuum on a rotary evaporator. For further purification and crystallisation, the product is dissolved in 100 ml. water and the pH adjusted to 2 with 1N hydrochloric acid. After 24 hours at 4° C., the precipitated crystals are filtered off, washed with a little cold water and dried in a vacuum at 40° C. Yield 2.3 g. (19% of theory).

TLC: (silica gel 60: ethyl acetate): RF=0.11.

UV spectrum (in 0.1M potassium phosphate buffer pH 7.0): $\lambda_{max}$=384 nm ($\epsilon$=18800 l/mol. cm.).

2)
2-Trifluoromethyl-4-nitrophenyl-2,3,4,6-tetra-O-acetyl-β-D-galactopyranoside

The preparation takes place from 2 g. (9.7 mmole) 2-trifluoromethyl-4-nitrophenol, 4.11 g. (10 mmole) acetobromogalactose and 2.32 g. (10 mmole) silver oxide analogously to Example 1.2. Yield 2 g. (38% of theory).

TLC (silica el 60; toluene/ethyl acetate 2:1 v/v): RF=0.35

3) 2-Trifluoromethyl-4-nitrophenyl-β-D-galactopyranoside 2.0 g. (3.7 mmole) of the acetylated compound from 2) are dissolved in 10 ml. anhydrous methanol and mixed with 4 ml. of a saturated solution of sodium methylate. The reaction mixture is stirred for 1 hour at 20° C., neutralised with acidic ion exchanger (Dowex 50 WX 8, H$^+$) and evaporated to dryness in a vacuum. Purification takes place by column chromatography on silica gel (elution agent chloroform/methanol 3:1 v/v). Yield 0.25 (18% of theory).

TLC (silica gel 60; chloroform/methanol 3:1 v/v): RF=0.5.

$^1$H-NMR (100 MHz, DMSO-d$_6$): δ (ppm)=8.50 (dd, J=3 Hz, 9 Hz, 1H), 8.39 (d, J=3 Hz, 1H), 7.58 (d, J=9 Hz; 1H), 5.30–5.05 (m; 1H), 5.03–4.83 (m; 1H), 4.80–4.55 (m; 2H), 3.82–3.40 (m; 6H).

EXAMPLE 3

Comparison of the substrates according to the present invention, 2-cyano-4-nitrophenyl-β-D-galactopyranoside (2-CN-4-NPG) and 2-trifluoromethyl-4-nitrophenyl-β-D-galactopyranoside (2-CF3-4-NPG), with the already known substrates 2-chloro-4-nitrophenyl-β-D-galactopyranoside (2-Cl-4-NPG) and 2-nitrophenyl-β-D-galactopyranoside (O-NPG).

1. Wavelengths of the absorption maxima of the chromogen and the associated extinction coefficients (ε).

TABLE 1

| chromogen | lambda max (nm) | ε (l/mol. cm.) |
|---|---|---|
| 2-Cl-4-nitrophenol | 405 | 16600 |
| 2-CN-4-nitrophenol | 376 | 15700 |
| 2-CF3-4-nitrophenol | 384 | 18800 |
| 2-nitrophenol | 408 | 2040 |

Measurement in 0.1 mole/l. potassium phosphate buffer (pH 7.0) at the absorption maximum of the chromogen.

2. Sensitivity comparison of the substrates and of their enzymatic cleavage rate.

The extinction change per minute (mE/min.) in the region of the absorption maximum (see Table 1) of the particular chromogen was determined with the use of identical amounts of the enzyme β-galactosidase: for the precise conditions see Example 4, II a) and b).

TABLE 2

| substrate | mE/min. | measurement wavelength (nm) |
|---|---|---|
| 2-Cl-4-NPG | 0.085 | 405 |
| 2-CN-4-NPG | 0.150 | 376 |
| 2-CF3-4-NPG | 0.109 | 384 |
| oNPG | 0.024 | 408 |

3. Evaluation in the T4/CEDIA (CEDIA with thyroxine T4 as hapten and monoclonal antibodies against thyroxine T4).

The test conditions are as in the following Example 4, I a) and b). The criterion for the evaluation of the individual substrates was the gradient of the calibration curve. This is determined in the manner described in Example 4, III a).

TABLE 3

| substrate | relative gradient | measurement wavelength (nm) |
|---|---|---|
| 2-Cl-4-NPG | 494 | 415 |
| 2-CN-4-NPG | 561 | 376 |
| 2-CF3-4-NPG | 528 | 376 |
| oNPG | 100 | 415 |

EXAMPLE 4

Investigation of substrate analogous for CEDIA tests

Methods

The following two test methods were used:
1) activity in the T4/CEDIA test
2) effectiveness as substrates for β-galactosidase.

I) Carrying out of the T4/CEDIA test

Definitions: EA=enzyme acceptor; ED=enzyme donor; EA$_{22}$=cloned enzyme acceptor for CEDIA; ED$_4$=cloned enzyme donor for CEDIA. The terms EA$_{22}$ and ED$_4$ are used according to U.S. Pat. No. 4,708,929. The amino acid sequences of these polypeptides are there disclosed.

a) Reagents

1) EA buffer

Monosodium dihydrogen phosphate (20 mmole/liter), disodium monohydrogen phosphate (30 mmole/liter), ethylene-bis-(oxyethylenenitrilo)-tetraacetic acid (EGTA) (18 mmole/liter), sucrose (25 mmole/liter), magnesium diacetate (9.67 mmole/liter), 4-morpholine-propanesulphonic acid (MOPS) (150 mmole/liter), sodium chloride (400 mmole/liter), L-methionine (10 mmole/liter), Pluronic L-101 (0.05%), Tween 20 (0.05%), hydroxypropyl-β-cyclodextrin (0.2%), dithiothreitol (DTT) (0.05 mmole/liter), sodium azide (23 mmole/liter); pH 7.4.

2) ED buffer

Monosodium dihydrogen phosphate (42 moles/liter), disodium monohydrogen phosphate (8 mmole/liter), sodium chloride (400 mmole/liter), MOPS (0.02 mmole/liter), EGTA (10 mmole/liter), Tween 20 (0.05%), Pluronic L-101 (0.05%), N-lauroylsarcosine (0.03%), DTT (0.05 mmole/liter), sodium azide (23 mmole/liter); pH 6.5.

3) EA reagent

Into EA buffer were introduced 546 U/ml. EA$_{22}$, 63 nmole/liter monoclonal antibody <T4> (commercially available, for example, from Western Chemical Research Corp., Denver, Colo., U.S.A., see U.S. Pat. No. 4,708,929) and 800 μmole/liter ANS (8-anilinonaphthalene-1-sulphonic acid ammonium salt).

ED reagent

Into ED buffer were introduced, as analyte, 115 nmole/liter ED$_4$- thyroxine T4 conjugate (preparation corresponding to ED-thyroxine conjugate according to U.S. Pat. No. 4,708,929) and the particular tested β-galactosidase substrate (1 mg./ml.).

b) Method

The T4/CEDIA was carried out on a Hitachi 704 Automatic Analyzer with the following amounts of reagent and under the given conditions:

| | |
|---|---|
| sample volume | 12 μl. |
| reagent 1 (ED₄-conjugate + substrate) | 235 μl. |
| reagent 2 (EA₂₂ = MAB) | 135 μl. |
| total volume | 382 μl. |
| measurement wavelength | 376/415 nm |
| temperature | 37° C. |

ΔE/min. was measured in the interval of 9–10 minutes.

II) Enzyme activity a) Reagents 1) 0.05M potassium phosphate buffer, pH 7.0
2) 10 mmole/liter magnesium chloride solution
3) 69.8% (v/v) mercaptoethanol solution
4) β-galactosidase (Boehringer Mannheim GmbH, order No. 105 031)
5) substrate, 5.9 mg./ml. in solution a)

b) Method

Pre-incubation: the following substances were pipetted into plastic cuvettes:

| | blank | sample |
|---|---|---|
| buffer (1) | 1100 μl. | 1100 μl. |
| magnesium chloride (2) | 150 μl. | 150 μl. |
| substrate (5) | 200 μl. | 200 μl. |
| mercaptoethanol (3) | 15 μl. | 15 μl. |

After mixing, the reaction was initiated:

| | | |
|---|---|---|
| buffer (1) | 25 μl. | — |
| β-galactosidase (4) | — | 25 μl. |

Δ/min. was calculated from the linear range.

III) Evaluation of the test results a) CEDIA test

Calibration curves were produced for all substrates. Of these curves, the gradients were compared.

$$\text{gradient} = \frac{\text{high calibrator rate} - \text{low calibrator rate}}{\text{conc. high calibrator} - \text{conc. low calibrator}}$$

Gradient expressed as percentage value of the 2-nitrophenyl-β-galactoside (=100%) for T4/CEDIA.

We claim:

1. A compound of the formula:

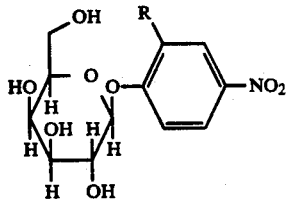

wherein R is a trifluoromethyl radical or a cyano group.

2. Reagent for the detection of an analyte in a sample solution with a CEDIA system using β-galactosidase as detection enzyme, wherein, as β-galactosidase substrate, it contains 2-trifluoromethyl-4-nitrophenyl-β-D-galactopyranoside and/or 2-cyano-4-nitrophenyl-β-D-galactopyranoside.

3. A process for the preparation of a compound of the formula I:

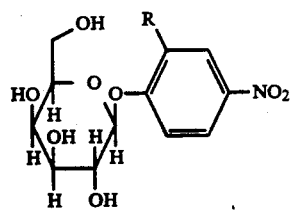

wherein R is a trifluoromethyl radical or a cyano group, comprising the steps of,
a) converting by nitration on the aromatic ring, a compound of the formula II:

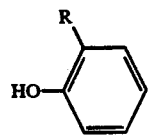

in which R is a trifluoromethyl radical or a cyano group, to produce a compound of the formula III:

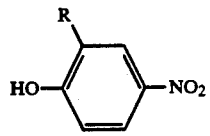

in which R has the same meaning as above,
b) reacting the compound of formula III with silver oxide to produce a reaction mixture,
c) then adding acetobromogalactose to the reaction mixture and stirring at ambient temperature to produce an acetylated intermediate, and
d) deacetylating the acetylated intermediate to produce a compound of formula I.

4. The process according to claim 3, wherein the compound prepared is 2-trifluoromethyl-4-nitrophenyl-β-D-galactopyranoside and wherein 2-trifluoromethylphenol is used as starting material.

5. The process according to claim 3, wherein the compound prepared is 2-trifluoromethyl-4-nitrophenyl-β-D-galactopyranoside and wherein 2-hydroxybenzonitrile is used as starting material.

6. A process for the detection of an analyte in a sample solution with a test system using β-galactosidase as a detection enzyme, comprising the steps of:
a) reacting β-galactosidase substrate, an enzyme acceptor for CEDIA, and an enzyme donor for CEDIA with a sample, wherein said β-galactosidase substrate is 2-trifluoromethyl-4-nitro-phenyl-β-D-galactopyranoside and/or 2-cyano-4-nitrophenyl-β-D-galactopyranoside,
b) measuring the hydrolysis of the β-galactosidase substrate, and
c) determining the presence of the analyte by the amount of hydrolysis.

7. The process according to claim 6 wherein said test system is a CEDIA system.

8. The process of claim 7, wherein the β-galactosidase consists of two polypeptide fragments which, when the two fragments are associated, are enzymatically active but which alone possess substantially no enzymatic activity.

* * * * *